United States Patent

Bruza et al.

Patent Number: 5,276,228
Date of Patent: * Jan. 4, 1994

[54] LIQUID BISARYLCYCLOBUTENE MONOMERS AND POLYMERS

[75] Inventors: Kenneth J. Bruza, Alma; Robert A. Kirchhoff, Midland, both of Mich.

[73] Assignee: The Dow Chemical Company, Midland, Mich.

[*] Notice: The portion of the term of this patent subsequent to Jul. 28, 2009 has been disclaimed.

[21] Appl. No.: 7,926

[22] Filed: Jan. 25, 1993

[51] Int. Cl.$^5$ .............................................. C07C 13/44
[52] U.S. Cl. ........................................ 585/25; 585/24; 585/26; 585/506
[58] Field of Search ............. 585/26, 25, 24, 506

[56] References Cited

U.S. PATENT DOCUMENTS

| | | | |
|---|---|---|---|
| 4,172,100 | 10/1979 | Tung et al. | 585/25 |
| 4,200,718 | 4/1980 | Tung et al. | 526/173 |
| 4,540,763 | 9/1985 | Kirchhoff | 526/281 |
| 4,642,329 | 2/1987 | Kirchhoff et al. | 526/284 |
| 4,661,193 | 4/1987 | Kirchhoff et al. | 156/307.3 |
| 4,687,823 | 8/1987 | Kirchhoff et al. | 526/284 |
| 4,783,514 | 11/1988 | Kirchhoff et al. | 526/281 |
| 4,812,588 | 3/1989 | Schrock | 556/453 |
| 4,831,172 | 5/1989 | Hahn et al. | 556/419 |
| 4,999,449 | 3/1991 | Kirchhoff | 560/8 |
| 5,134,214 | 7/1992 | Bruza et al. | 526/262 |

*Primary Examiner*—Joseph L. Schofer
*Assistant Examiner*—Mark Nagumo
*Attorney, Agent, or Firm*—Lynn M. Zettler

[57] ABSTRACT

This invention is directed to a class of arylcyclobutene monomers having the general formula:

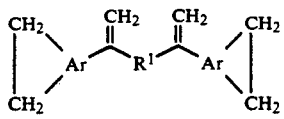

wherein
Ar is aromatic, with the proviso that the carbons of the cyclobutene rings are bonded to adjacent carbon atoms on the same aromatic ring of Ar;
and $R^1$ is a divalent alkyl, cycloaliphatic, aromatic, heteroaromatic, or heterocyclic moiety;

polymeric compositions containing these monomers; and articles containing said polymeric compositions.

6 Claims, No Drawings

LIQUID BISARYLCYCLOBUTENE MONOMERS AND POLYMERS

STATEMENT OF INVENTION

This invention relates to liquid bisarylcyclobutene monomers, polymeric compositions obtained from said liquid monomers and their use in composites and microelectronic applications such as multichip modules. These liquid monomers are advantageous in that they do not require processing prior to polymerization as other bisarylcyclobutene monomers do.

BACKGROUND OF INVENTION

Bisbenzoeyclobutene compounds are known and exemplified in U.S. Pat. No. 4,540,763. One such compound:

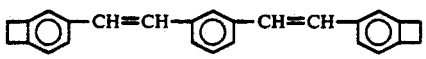

can be made by the reaction of bromobenzocyclobutene with m-divinylbenzene to produce a solid product having a melting point of 150°-152° C. The monomers disclosed in U.S. Pat. No. 4,540,763 are useful in preparing thermoset and thermoplastic polymeric compositions. While these compositions exhibit excellent thermal stability and chemical resistance and have uses as films, coatings, adhesives, fiber-reinforced plastics, composites, structural laminates and other engineering applications, they have the undesirable feature in that they are solids at room temperature and require processing prior to polymerization processes. They must be dissolved in a solvent, processed from the melt of the monomer or subjected to B-staging (partial conversion to higher molecular weight) to yield an amorphous lower melting solid that has increased viscosity necessary for processing.

Liquid bisbenzocyclobutene monomers bridged by a polyorganosiloxane group are disclosed in U.S. Pat. No. 4,812,588. These monomers can be prepared by reacting a bromobenzocyclobutene with the desired organopolysiloxane bridging group and are particularly useful for electronic applications. Although these monomers are liquid as isomeric mixtures, they are not liquids in their pure form.

It would be useful to have bisarylcyclobutene monomers which are liquid at room temperature and produce thermally stable polymers with good physical and mechanical properties.

It would also be desirable to have liquid bisarylcyclobutene monomers having a variety of bridging groups for use as homopolymers, comonomers in polymeric compositions or reactive diluents with other monomers. It would also be desirable to have polymeric compositions of these monomers for use in advanced composites and microelectronics.

SUMMARY OF INVENTION

This invention is directed to a class of arylcyclobutene monomers having the general formula:

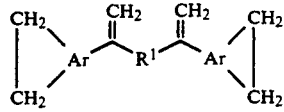

wherein
Ar is aromatic, with the proviso that the carbons of the cyclobutene rings are bonded to adjacent carbon atoms on the same aromatic ring of Ar;
and $R^1$ is a divalent alkyl, cycloaliphatic, aromatic, heteroaromatic, or heterocyclic moiety;
polymeric compositions containing these monomers; and articles containing said polymeric compositions.

The bisarylcyclobutene monomers of this invention may be liquids at room temperature and therefore do not require further treatment such as dissolving in a solvent, processing from a melt, or B-staging prior to polymerization processes. These monomers are also useful as reactive diluents for other benzocyclobutene monomers and in the preparation of a wide range of polymeric compositions. These monomers may also be used as matrix resins by themselves or can be copolymerized with other thermally stable comonomers such as bismaleimides to provide thermally stable, moisture resistant copolymers. They would be most attractive to the area of resin transfer molding.

The bisarylbenzocyclobutene compounds of this invention may also be partially polymerized(B-staged), wherein the compound is in a polymerized yet uncured form and contains reactive polymerization sites. Partial thermal polymerization of the bisarylcyclobutene compound forms a prepolymer which may have more desirable properties in use, such as a wider temperature range between the melting point and the cure temperature and a more desirable viscosity. The prepolymer retains its solubility in organic solvents because it is not polymerized to the gel point. The prepolymer may retain its density and shrinks less than the monomer upon curing. The prepolymer can be employed to prepare cured polymeric compositions.

The prepolymer contains both reacted and unreacted polymerization sites. It may contain completely unreacted bisarylcyclobutene compound, oligomers and cured polymer as well as other unreacted materials included in the bisarylcyclobutene compound.

In one method of forming the prepolymer by partial thermal polymerization, an amount of the bisarylcyclobutene compound is heated to a temperature sufficient to initiate and sustain polymerization. Bisarylcyclobutene compounds may also be partially polymerized with any type of radiation such as X-ray or E-beam or in any way that will lead to polymerization.

Partial thermal polymerization may be effected over a wide range of temperatures. The lower the temperature the longer the process will take. Partial thermal polymerization takes place at a temperature effective to polymerize the bisarylcyclobutene compound. Such a temperature is preferably above 150° C. and below 220° C. The reaction mixture is removed from the heat after it attains an appropriate viscosity which is greater than the initial viscosity of the bisarylcyclobutene compound and which enables more effective use of the partially polymerized composition.

The viscous, partially thermally polymerized composition can be employed as a film wherein an effective amount of the neat partially polymerized composition is applied to a surface, and subsequently further polymerized. Or, the partially polymerized composition can be mixed with a suitable solvent. The solution can then be applied to a surface, the solvent evaporated, and the partially polymerized composition further polymerized to provide a polymer film.

Polymeric compositions obtained from these bisarylcyclobutene monomers are useful in advanced composites, high performance adhesives and microelectronic applications. These polymeric compositions are low moisture absorbing, and show thermal and thermooxidative stability. In particular, homopolymers of the above monomers are useful in multichip modules, inner layer dielectric coatings, and in E-beam lithography.

DETAILED DESCRIPTION OF INVENTION

The bisarylcyclobutene monomers of this invention are monomers containing at least two vinyl moieties within the bridging group and having the general formula:

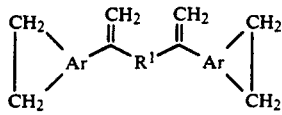

wherein
Ar is aromatic, with the proviso that the carbons of the cyclobutene rings are bonded to adjacent carbon atoms on the same aromatic ring of Ar;
and $R^1$ is a divalent alkyl, cycloaliphatic, aromatic, heteroaromatic, or heterocyclic moiety.

The bisarylcyclobutene monomers of this invention have melting points of less than 30° C. in their pure form. Preferably, the melting points are less than 25° C. and most preferably, less than 20° C.

The term alkyl refers to straight or branched, saturated hydrocarbon chains containing 1-6 carbon atoms. The preferred alkyl groups are ethyl, butyl, propyl and isopropyl.

The term cycloaliphatic refers to a saturated or partially unsaturated ring structure containing only carbon and hydrogen atoms. The preferred ring structures contain 5-12 carbon atoms, more preferred ring structures contain 6-9 carbon atoms, and the most preferred is cyclohexane.

The term aromatic refers to a group of unsaturated cyclic hydrocarbons containing one or more rings, which contain $(4n+2)\pi$ electrons as described in Morrison & Boyd, *Organic Chemistry*, 3rd ed., 1973. The preferred aromatics are benzene, naphthalene, anthracene, phenanthrene, indene, indane, dihydronaphthalene, and tetrahydronaphthalene; the most preferred being benzene.

The term heteroaromatic refers to structures having an aromatic ring containing at least one atom which is other than carbon. Examples of heteroaromatics include but are not limited to pyrrole, pyran, pyrazine, thiophene, pyridine, pyrimidine, furan, and purine. The preferred heteroaromatics are pyridine, thiophene and furan.

The term heterocyclic refers to a saturated or partially unsaturated closed ring structure in which one or more of the atoms in the ring is an element other than carbon. Examples of heterocyclics include but are not limited to tetrahydropyran, tetrahydrothiopyran, piperidine, piperazine, tetrahydrofuran and tetrahydrothiophene.

The term hydrocarbon includes any organic compound containing exclusively carbon and hydrogen atoms, e.g. alkyl, cycloaliphatic and aromatic.

The preferred monomers are all hydrocarbon monomers wherein $R^1$ is a divalent alkyl, cycloaliphatic or aromatic moiety. The more preferred monomers are all hydrocarbon monomers wherein $R^1$ is a divalent aromatic moiety. The most preferred monomer is 3,3'-(1,3-phenylenedi-2,1-ethenediyl) bisbicyclo(4.2.0)octa-1,3,5-triene having the formula:

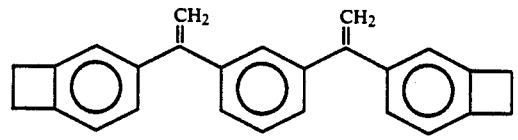

Monomer Synthesis

The bisarylcyclobutene monomers of this invention, wherein $R^1$ is a divalent aromatic or heteroaromatic moiety, can be prepared in several ways. A typical preparation is by reacting a diketone bisarylcyclobutene of the formula:

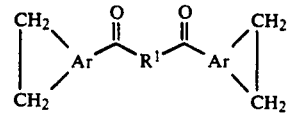

wherein
$R^1$ is a divalent aromatic or heteroaromatic moiety, and
Ar is aromatic, with the proviso that the carbons of the cyclobutene rings are bonded to adjacent carbon atoms on the same aromatic ring of Ar;
with a Grignard reagent, e.g. methyl magnesium bromide, in the presence of a solvent, to form a tertiary carbinol of the formula:

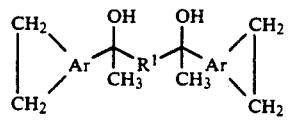

wherein
$R^1$ is a divalent aromatic or heteroaromatic moiety, and
Ar is aromatic, with the proviso that the carbons of the cyclobutene rings are bonded to adjacent carbon atoms on the same aromatic ring of Ar;
followed by acid catalyzed elimination of water using e.g. toluenesulfonic acid, to yield a compound of the general formula:

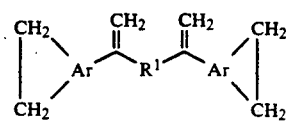

wherein
$R^1$ is a divalent aromatic or heteroaromatic moiety, and

Ar is aromatic, with the proviso that the carbons of the cyclobutene rings are bonded to adjacent carbon atoms on the same aromatic ring of Ar.

The reaction of the methylmagnesium bromide with the diketone can be carried out with an excess of the Grignard reagent but it is preferred that the stoichiometry of the reaction be two moles of Grignard reagent to one mole of the diketone. The reaction can be carried out in either ethereal solvents such as diethyl ether, tetrahydrofuran or diglyme; or in hydrocarbon solvents such as toluene or benzene. The preferred solvent is tetrahydrofuran.

The reaction is run for one hour at 67° C. The reaction could also be carried out at room temperature or lower but would require a longer period of time for complete reaction to occur. The preferred reaction temperature is at the boiling point of tetrahydrofuran (67° C.), but the temperature range could be anywhere between 0° C. to 130° C. with the time of reaction either becoming greater or shorter depending upon the temperature. The temperature range is therefore 0° C. to 150° C. and the preferred temperature range being between room temperature and 80° C. and the most preferred temperature range being 50°-70° C.

The dehydration reaction is run with the dicarbinol dissolved in an excess of an aromatic solvent, providing a dilute solution. The concentration of the dicarbinol can range from 0.05-1.0 moles per liter of solvent. The preferred range is between 0.05-0.5 moles per liter and the most preferred range is from 0.05-0.2 moles per liter.

The reaction is run with a small amount of para toluene sulfonic acid as the catalyst. The concentration of the catalyst relative to the dicarbinol can be from 0.1 to 20 mole percent. The preferred range of catalyst is from 0.5 to 3.0 mole percent and the most preferred range is from 1.0 to 3.0 mole percent.

The bisarylcyclobutene monomers of this invention wherein $R^1$ is a divalent alkyl, cycloaliphatic or heterocyclic moiety, can be prepared in several ways. A typical method includes using a Wittig reaction as reported by Maryanoff et.al., *Chem. Rev.*, 89(4) pgs. 863-927(1989). A typical preparation includes reacting a diketone bisarylcyclobutene of the general formula:

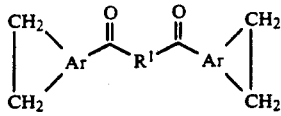

II wherein
$R^1$ is a divalent alkyl, cycloaliphatic or heterocyclic moiety, and
Ar is aromatic, with the proviso that the carbons of the cyclobutene rings are bonded to adjacent carbon atoms on the same aromatic ring of Ar;
with methylenetriphenylphosphine to yield a compound of the general formula:

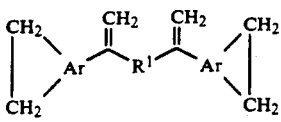

I wherein $R^1$ is a divalent alkyl, cycloaliphatic or heterocyclic moiety, and
Ar is aromatic, with the proviso that the carbons of the cyclobutene rings are bonded to adjacent carbon atoms on the same aromatic ring of Ar.

The diketone bisarylcyclobutene of Formula II may be made by reacting 2 equivalents of an arylcyclobutene of the general formula:

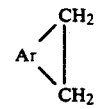

wherein Ar is aromatic, with the proviso that the carbons of the cyclobutene rings are bonded to adjacent carbon atoms on the same aromatic ring of Ar;
with one equivalent of a diacid chloride of the general formula:

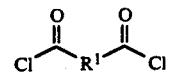

IV wherein $R^1$ is a divalent alkyl, cycloaliphatic, aromatic, heteroaromatic, or heterocyclic moiety,
in the presence of a Lewis acid. An example of the synthesis of a bisarylcyclobutene, e.g. the compound of Formula II wherein Ar and $R^1$ are each phenyl, is found in U.S. Pat. No. 4,999,449 which is incorporated herein by reference.

Polymer Synthesis

The polymeric compositions of this invention can be prepared by heating at least one monomer as described above to a temperature sufficient for polymerization to occur. A typical polymerization process comprises heating the monomeric composition to 160° C. for 1 hour, 200° C. for 2 hours, and 250° C. for 1 hour. Polymeric compositions may also be obtained by copolymerizing at least one monomer as described above with at least one additional monomer such as a bismaleimide or another bisbenzocyclobutene.

The polymeric compositions prepared may be characterized in that they contain multiple units of the general structure:

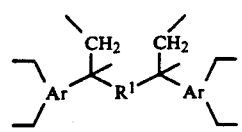

V wherein
Ar is aromatic, with the proviso that the carbons of the cyclobutene rings are bonded to adjacent carbon atoms on the same aromatic ring of Ar;
and $R^1$ is a divalent alkyl, cycloaliphatic, aromatic, heteroaromatic, or heterocyclic moiety;
within the polymeric backbone.

The most preferred polymer is the homopolymer of 3,3'-(1,3-phenylenedi-2,1-ethenediyl) bisbicyclo(4.2.0)octa-1,3,5-triene.

The following examples are included as representative methods and compounds and do not limit the scope of the invention or the claims.

Example 1 - Preparation of 3,3'-(1,3-phenylenedi-2,1-ethenediyl) bisbicyclo(4.2.0)octa-1,3,5-triene A. Preparation of α,α'-(1 3-phenylene) bis-(α-methyl bicyclo(4.2.0)octa-1,3,5-trien-3,3'-ethanol)

Into a 1L, 3-necked roundbottom flask equipped with a magnetic stirring bar, an equilibrating addition funnel with a rubber septum, and a reflux condenser with a nitrogen inlet is placed 50 g (0.1478 mol) of bis (4-benzocyclobutenyl)-1,3-phenylene diketone and 400 mL of dry tetrahydrofuran. The mixture is brought to a gentle reflux under nitrogen. As the temperature nears the reflux temperature all of the diketone dissolves in the solvent. The addition funnel is charged with 108.4 mL of methylmagnesium bromide (3m in diethyl ether; 0.2958 mol; 35.72 g). Methylmagnesium bromide is then added dropwise and the reaction mixture is refluxed for 1 hour after the addition is complete. Heating is stopped and the reaction mixture is cooled to 5° C. using an ice bath. The addition funnel is charged with 75 mL of 1N HCl and the acid is added dropwise to the stirring reaction mixture. Upon completion of the HCl addition, the two phase, yellow reaction mixture is transferred to a separatory funnel and diethyl ether (400 mL) is added. The aqueous layer is separated from the organic layer. The aqueous layer is extracted with diethyl ether (1×200 mL) and the organic phases are combined. The organic layer is then washed with 10% HCl (4×200 mL); distilled water (4×200 mL); and saturated NaCl (2×200 mL). The organic layer is then dried over MgSO4 and filtered through "Celite". The volatiles are removed on a rotary evaporator and 51.87 g of a viscous amber fluid is obtained (yield=94.8%).

B. Dehydration of α,α'-(1,3-phenylene) bis-(α-methyl bicyclo(4.2.0)octa-1,3,5-trien-3,3'-ethanol) to yield 3,3'-(1,3-phenylenedi-2,1-ethenediyl) bisbicyclo(4.2.0)octa-1,3,5-triene Into a 5L 3-necked flask equipped with a magnetic stirring bar, two stoppers, a Dean Stark Trap with reflux condenser and nitrogen inlet, is placed 51.87 g (0.1401 mol) of α,α'-(1,3-phenylene) bis-(α-methyl bicyclo(4.2.0)octa-1,3,5-trien-3,3'-ethanol) and 2000 mL of dry toluene. The solution is heated to a gentle reflux and 0.423 g (2.22×10$^{-3}$ mol) of para toluenesulfonic acid is added in one portion. The reaction mixture is then vigorously refluxed for two minutes and returned to a regular gentle reflux. The reaction is heated at reflux for 1.5 hours with the constant removal of water in the Dean Stark Trap. Heating is then stopped and the reaction is cooled to room temperature. The reaction mixture is then transferred to a separatory funnel and the organic phase is washed with 1M NAOH (2×200 mL); distilled water (3×200 mL); and saturated NaCl (2×200 mL). The organic phase is then dried over MgSO4 and filtered through "Celite". The volatiles are removed on a rotary evaporator and 62.4 g of a thick viscous amber liquid is obtained. The product is purified by column chromatography upon silica gel (500 g) with n-hexane as the mobile phase to obtain 39.65 g of an opaque white liquid (yield=85%).

Example 2—Preparation of homopolymer of 3,3'-(1,3-phenylenedi-2,1-ethenediyl) bisbicyclo(4.2.0)octa-1,3,5-triene Into a glass test tube with a 14/20 ground glass joint, is placed 0.91 g (2.72×10$^{-3}$ mol) of 3,3'-(1,3-phenylenedi-2,1-ethenediyl) bisbicyclo(4.2.0)octa1,3,5-triene. A nitrogen inlet is added to the tube and the monomer is placed under a positive flow of nitrogen. The tube is placed into a 160° C. oil bath. The following heating schedule is then followed: 160° C./1 hour; 200° C./2 hour; and 250° C./1 hour. At the end of this time the tube is removed from the bath at 250° C. and rapidly cooled to room temperature. The tube is then broken and the polymer removed as a homogeneous cylindrical piece which is opaque amber in color.

What is claimed is:

1. A compound of the formula:

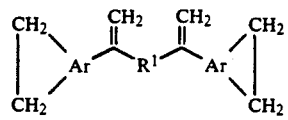

wherein

Ar is aromatic, with the proviso that the carbons of the cyclobutene rings are bonded to adjacent carbon atoms on the same aromatic ring of Ar;

and R$^1$ is a divalent alkyl, cycloaliphatic, aromatic, heteroaromatic, or heterocyclic moiety.

2. The compound of claim 1 having a melting point of less than 25° C.

3. The compound of claim 1 wherein Ar is benzene.

4. The compound of claim 3 wherein R$^1$ is a divalent aromatic moiety.

5. The compound of claim 4 wherein R$^1$ is selected from the group comprising benzene, naphthalene, anthracene, phenanthrene, indene, indane, dihydronaphthalene, or tetrahydronaphthalene.

6. The compound of claim 5 having the formula:

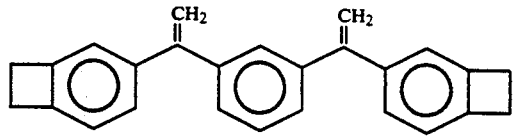

* * * * *